United States Patent [19]

Ito et al.

[11] Patent Number: 5,506,151

[45] Date of Patent: Apr. 9, 1996

[54] NON-SPECIFIC REACTION SUPPRESSOR

[75] Inventors: Michio Ito, Indianapolis, Ind.; Satoshi Sugawa, Machida, Japan; Atsushi Yanagida, Carmel, Ind.

[73] Assignee: Mitsubishi Kasei Corporation, Tokyo, Japan

[21] Appl. No.: 194,475

[22] Filed: Feb. 9, 1994

[51] Int. Cl.$^6$ .................................. G01N 33/546
[52] U.S. Cl. .................. 436/533; 436/518; 436/815; 436/826
[58] Field of Search ...................... 436/533, 826, 436/518, 815

[56] References Cited

FOREIGN PATENT DOCUMENTS 2042170  9/1980  United Kingdom .

OTHER PUBLICATIONS

J. Polanec et al., Journal of Clinical Laboratory Analysis, vol. 8, pp. 16–21 (1994).

M. Devey et al., Journal of Immunological Methods, vol. 106, pp. 119–125 (1988).

D. Hogben et al., Journal of Immunological Methods, vol. 93, pp. 29–36 (1986).

H. Thomas et al., Journal of Virological Methods, vol. 31, pp. 219–228 (1991).

M. Greenwood et al., Epidemiol. Infect., vol. 104, pp. 345–350 (1990).

Primary Examiner—Mary E. Ceperley
Attorney, Agent, or Firm—Oblon, Spivak, McClelland, Maier & Neustadt

[57] ABSTRACT

A non-specific reaction suppressor for immunoassays having the formula:

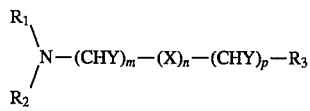

where $R_1$, $R_2$, Y, X, and $R_3$ are defined in the specification.

16 Claims, 7 Drawing Sheets

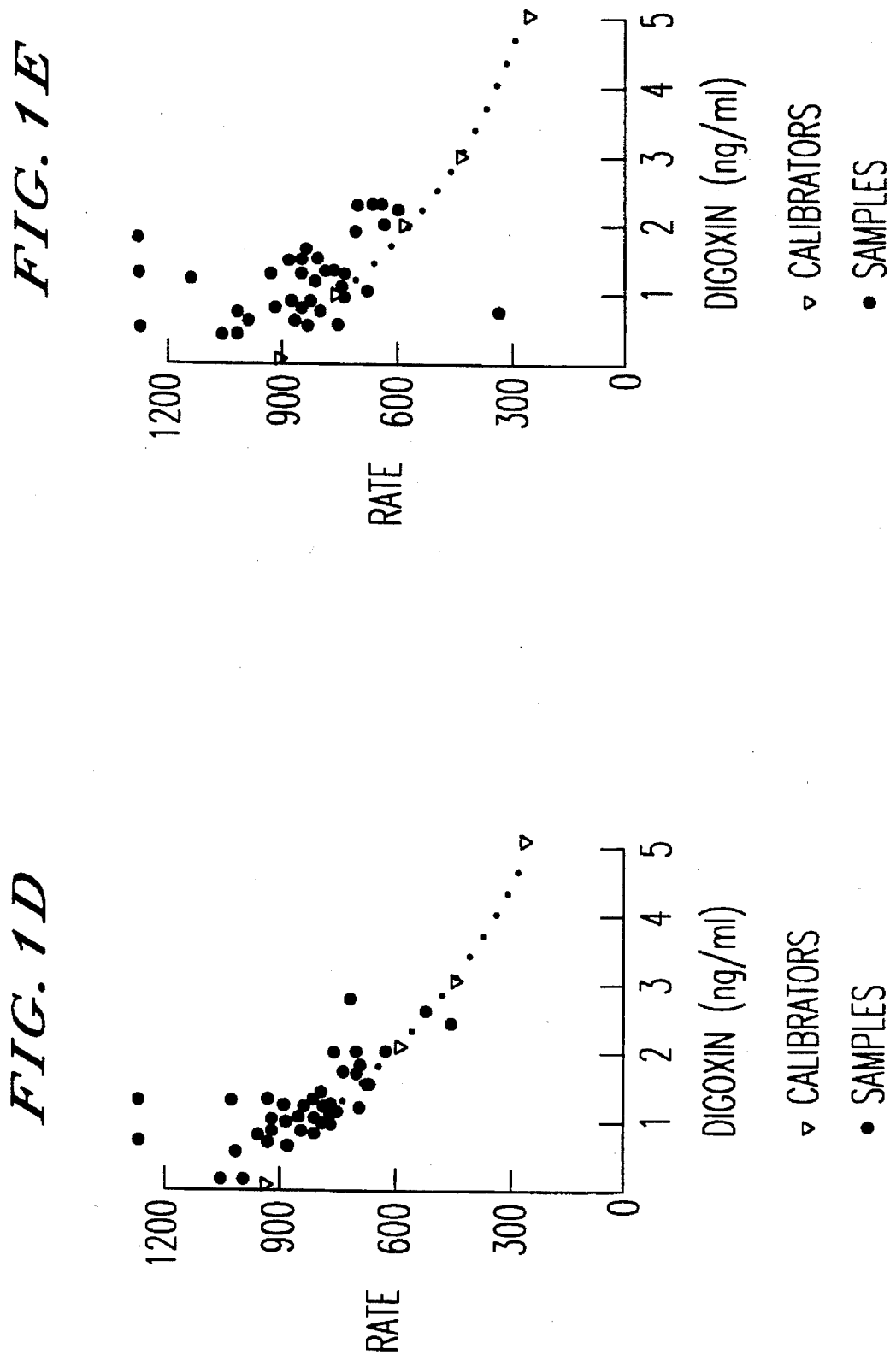

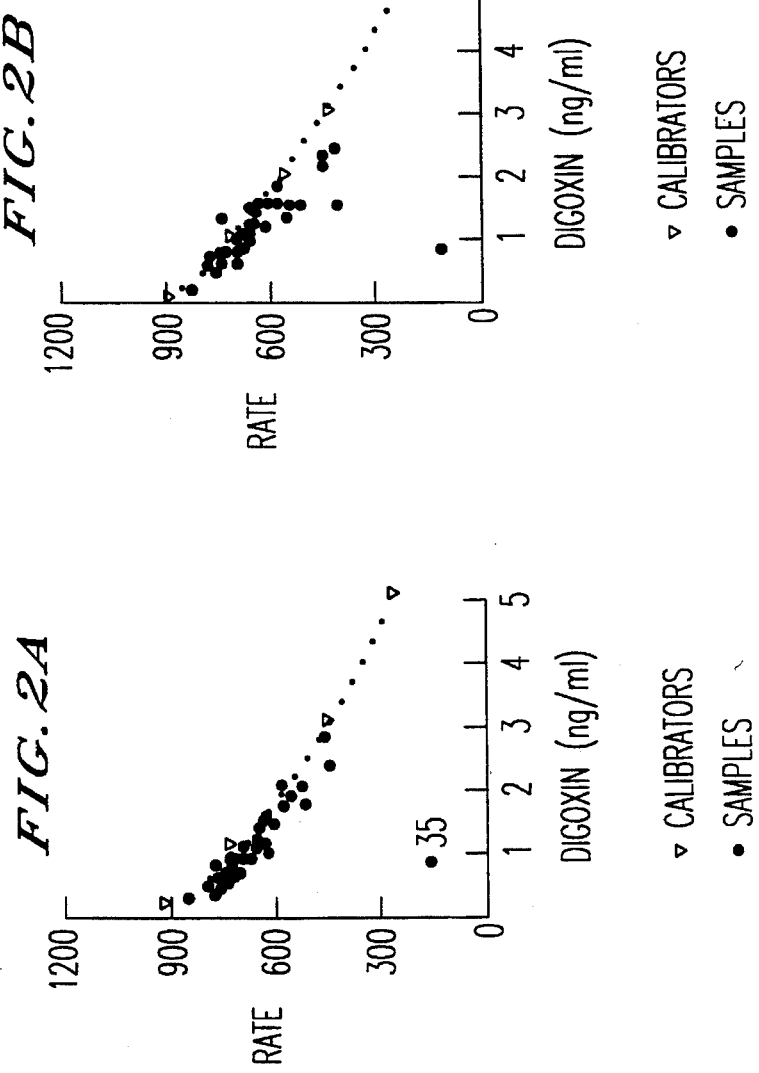

1-ETHYL-3-(3-DIMETHYLAMINOPROPYL)UREA

N,N-DIMETHYLETHYLAMINE

DIMETHYLAMINE

3-DIMETHYLAMINOPROPYLAMINE

DIETHYLAMINE

3-DIETHYLAMINOPROPYLAMINE

DIPROPYLAMIME

DIMETHYLAMINOPROPYLCHLORIDE 1,3-DIAMINOPROPANE $NH_2CH_2CH_2CH_2NH_2$ 1,3-DIAMINO-2-PROPANOL 1,3-BIS(DIMETHYLAMINO)-2-PROPANOL

NON-SPECIFIC REACTION SUPPRESSOR

BACKGROUND OF THE INVENTION

1. Field of the Invention

The present invention relates to a non-specific reaction suppressor for immunoassays. More specifically, the present invention relates to secondary and tertiary amines which, when added to an immunoassay, improve the accuracy and reliability of the quantitative determination of the extent of immunoreactant-complementary immunoreactant interaction by significantly reducing or eliminating non-specific interactions.

2. Discussion of the Background

Immunoassays are techniques for the detection and/or quantitation of antigens, antibodies, etc. and are well known in the art. Immunoassays are described in the *Handbook of Experimental Immunology*, Vols. 1–4, Blackwell Scientific, incorporated herein by reference. U.S. Patents describing immunoassays include U.S. Pat. Nos. 4,203,724, 4,590,156, 4,716,123, 4,772,550, 4,851,329, 4,960,692 and 5,100,805, all incorporated herein by reference.

Non-labeled immunoassays have limited sensitivity since large antigen-antibody complexes must be formed for their detection. Examples of non-labeled reagent assays include immunoprecipitation methods, agglutination methods and light scattering techniques. Labeled reagent immunoassays include reagents labeled with radioisotopes, fluorophores, etc.

Immunoassays are broadly divided into two general groups: reagent observed and analyte observed (see Ekins, R., *Immunoassay for the Eighties*, University Press, Baltimore, Md, 1981, incorporated herein by reference). In reagent observed immunoassays an analyte to be detected and a complementary immunoreactive species present in excess are brought together. Examples include sandwich assays, etc. In analyte observed immunoassays, the analyte to be determined is labeled and is present in excess. Radioimmunoassays (RIA) represent a form of this type of assay wherein the analyte is labeled with a radioisotope.

Enzyme immunoassays (EIAs) measure the immunoreactant-complementary immunoreactant (i.e., antigen-antibody) reaction using enzyme reaction measurements. Recently EIAs have experienced rapid growth in the clinical laboratory due, in part, to the lack of a need for radioisotopes. Current EIA methods include homogeneous assays which do not include a separation step (because signal modulation occurs following immunoreactant-complementary immunoreactant reaction).

While immunoassays are generally classified on the basis of which immunoreactant (antigen or antibody) is determined, which reactant is labeled, whether competitive or non-competitive methods are used and which method of separation of bound and free reactants (if any) is used, all immunoassays rely, eventually, upon the formation of at least one immunoreactant-complementary immunoreactant complex.

Immunoassays are designed to detect, monitor and/or quantitate this complex formation and, preferably, provide a means by which the amount of a target species in a given sample is determined. To effect complex formation, generally an immunoreactant is bound to the surface of a bead, plate, etc., which surface is then brought into contact with a solution of complementary immunoreactant. The immobilization of immunoreactants on solid supports is well known in the art and described in, e.g., *Immobilized Affinity Ligand Techniques*, by G. T. Hermanson, et al, 1992, and U.S. Pat. Nos. 4,203,724, 4,716,123, 4,772,550, 4,851,329, 4,960,692 and 5,100,805, all incorporated herein by reference.

While the sensitivity of immunoassays has made them popular techniques in the determination of analytes, immunoassays, in addition to the desired immunoreactant-complementary immunoreactant reaction described above, undergo non-specific reactions which interfere with the determination of an analyte's presence and/or concentration. These non-specific reactions are well known in the art and are described in, e.g., L. M. Boscato et al, *Clin. Chem.*, 32/8, 1986; H. C. Vaidya et al, *Clin. Chem.*, 38/9, 1992; and C. Chang et al, *Clin. Chem.*, 33/6, 1987, all incorporated herein by reference. Non-specific reactions may arise from non-analyte antibody-binding substances present in the sample being tested, from the interaction of labeled or non-labeled analyte with the solid immunoreactant support, etc. In the past, bovine serum albumin, etc. has been used to minimize non-specific interactions. However, non-specific reactions remain a problem in immunoassay techniques.

SUMMARY OF THE INVENTION

One object of the present invention is to provide a method for suppressing and eliminating non-specific reactions occurring in immunoassays.

Another object of the present invention is to provide an analyte solution containing a non-specific immunoreaction suppressor.

Another object of the present invention is to provide a composition comprising solvent, a non-specific reaction suppressor and a solid support having attached thereto an immunoreactant.

Another object of the present invention is to provide a solid support having coated on the surface thereof an immunoreactant and a non-specific reaction suppressor.

Another object of the present invention is to provide a diagnostic kit comprising a non-specific reaction suppressor and an immunoreactant.

A more complete appreciation of the invention, its objects and many of the attendant advantages thereof will be readily obtained as the same becomes better understood by reference to the following detailed description.

BRIEF DESCRIPTION OF THE DRAWINGS

FIGS. 1A–1E show the results of the agglutination immunoassay determination of digoxin in the absence of the invention non-specific reaction suppressor. Data is spread over five graphs for ease of viewing.

FIGS. 2A–2E show the data distribution for the agglutination immunoassay determination of the same digoxin samples tested in FIG. 1 in the presence of a non-specific reaction suppressor according to the invention. The kit according to the present invention comprises first and second containers, the first container containing a solid support sensitized with an immunoreactant, the second container containing the above-described non-specific reaction suppressor.

DESCRIPTION OF THE PREFERRED EMBODIMENTS

Figure 1A:
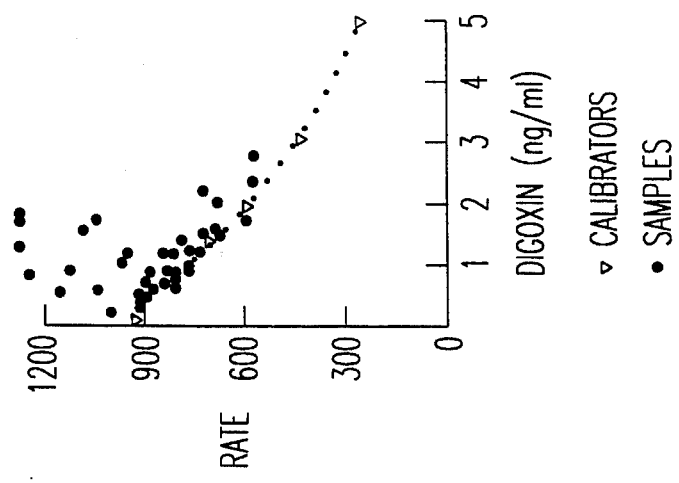
Figure 1B:
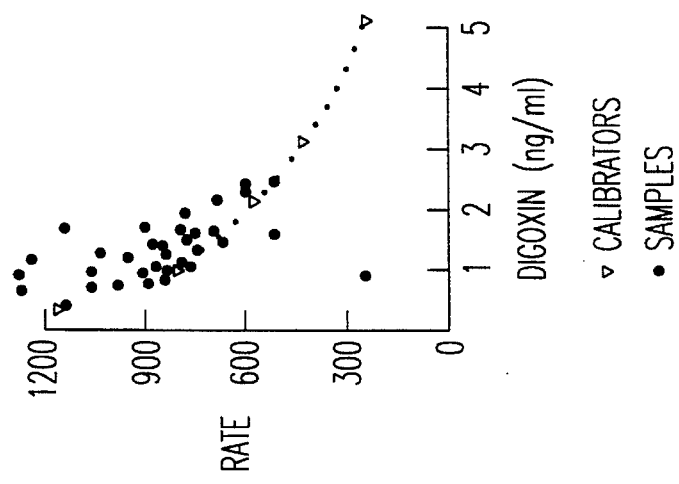
Figure 1C:
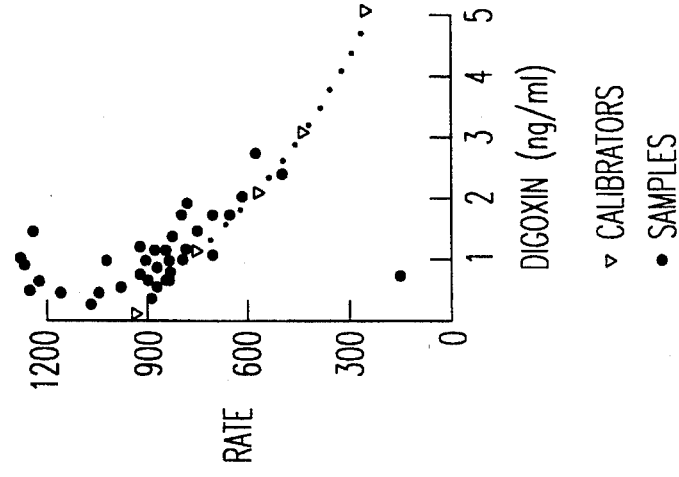
Figure 2E:
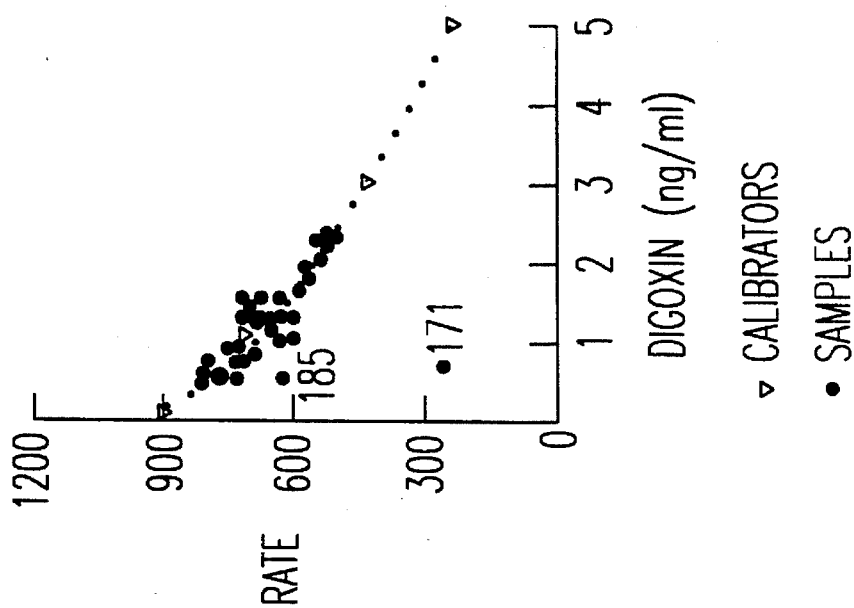
Figure 2D:
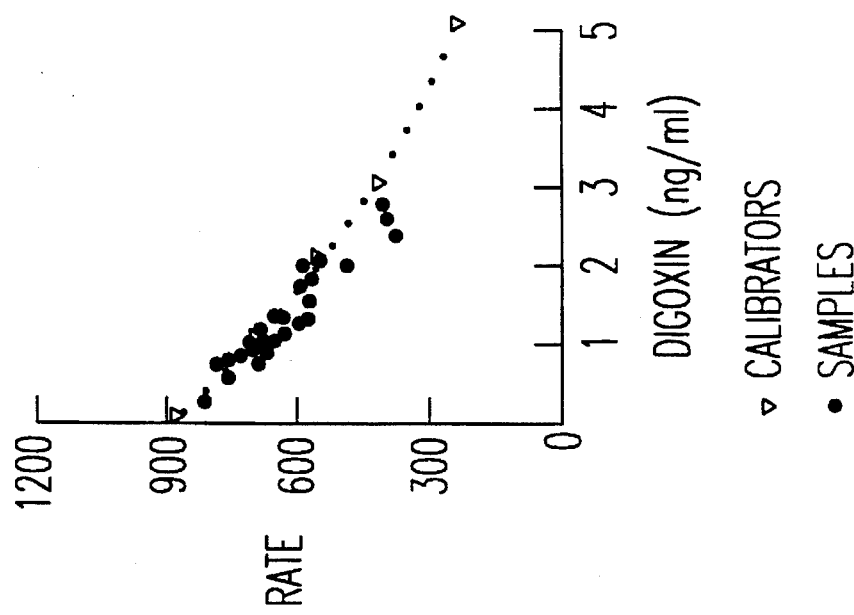

The present invention is directed to secondary and tertiary amine non-specific reaction suppressors of the formula:

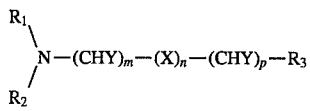

wherein X is —NH—(CO)—NH—, —NH—(CS)—NH—, or —N=C=N—, $R_1$ and $R_2$, which may be the same or different, are $C_1$-$C_5$ linear or branched alkyl groups, or $R_1$ and $R^2$, together with nitrogen, is

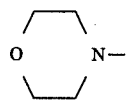

or the metho-p-toluenesulfonate salt thereof,

Y, which may be the same or different, is any of H, OH and halogen (Br, Cl, F), $R_3$ is —$NR_1R_2$, —$NH_2$, —CHY, cyclohexyl, or H, m is an integer of from 0 to 5, p is an integer of from 0 to 5, and n is 0 or 1, provided that at least one of m and p is at least 1 when n equals 1, and provided that when m=n=P=0, $R_3$ is H or —$CH_2Y$, and the acid addition salts thereof, particularly the HCl salts, phosphoric acid salts and sulfuric acid salts thereof.

These secondary and tertiary amines may be substituted on any or all of the m and p methylenes with any combination of H, OH and halogen, include compounds where m=n=p=0 and $R_3$ is, e.g., H or methyl, compounds where m, optionally n and optionally p are not 0 and $R_3$ is H or —CH 2Y, etc.

Several of the above-described compounds are the hydrolysis products of carbodiimides useful in the preparation of peptides. See Sheehan, J. C., et al, *J. Org. Chem.*, 26, 2525, 1961 and Staros, J. V., et al, *Anal. Biochem.*, 156, 220, 1986, both incorporated herein by reference. One particularly preferred non-specific reaction suppressor is 1-ethyl-3-(3-dimethylaminopropyl)urea (EDU), i.e., a compound according to the formula above where $R_1$= $R_2$= methyl, Y=H, m=3, n=1, p=1 and $R_3$=methyl. Another is 1-cyclohexyl-3-(2-morpholinoethyl) carbodiimide metho-p-toluenesulfonate (CMC). These compounds and their hydrolysis products are useful for suppressing non-specific reactions in immunoassays, particularly immunoassays wherein an immunoreactant is attached covalently or by adsorption to a solid support.

The invention non-specific reaction suppressors are generally commercially available and prepared by simple organic reactions well known to those of ordinary skill in this art and explained in, e.g., *Introduction to Organic Chemistry*, A. Streitwieser and C. Heathcock, Macmillan, 1976; *Reagents for Organic Synthesis*, Feiser and Fieser, John Wiley and Sons, 1967 and succeeding volumes; *Survey of Organic Syntheses*, John Wiley and Sons, Vols I and II, 1970; and *Advanced Organic Chemistry*, March, Wiley, 1985, all incorporated herein by reference. For example, the urea compounds (—NH—CO—NH—) can be prepared by hydrolysis of the carbodiminde (—N=C=N—) compounds.

The non-specific reaction suppressor of the present invention described by the above formula may be used singly or in combination and may be added to the sample to be tested (i.e., analyte) or to the known immunoreactant optionally adsorbed or covalently bound to a solid support. Further, the non-specific reaction suppressor can be utilized in combination with conventional non-specific reaction suppressors such as bovine serum albumin.

A particularly preferred embodiment of the present invention is one where a compound according to the above formula is used to suppress non-specific immunoassay reactions in which an immunoreactant has first been bound to a substrate using a carbodiimide reagent such as 1-ethyl-3-(3-dimethylaminopropyl)-carbodiimide hydrochloride (EDC) or CMC. A further preferred embodiment of the present invention is one where the non-specific reaction suppressor utilized is the hydrolysis product of the carbodiimide used in the binding of the immunoreactant to the solid support.

The amount of non-specific reaction suppressor useful for suppressing non-specific immunoassay reactions according to the invention is from 0.1 to 300 mM, preferably 0.5 to 50 mM, more preferably 1.25 to 25 mM based on the total immunoassay solution volume, the solution volume of a sample to be tested, or the solution volume of a solid support sensitized with immunoreactant suspended in a solvent.

The non-specific reaction suppressor of the present invention is added to either or both of the immunoreactant and the analyte being determined prior to complex formation and, when added to an immunoreactant adsorbed or covalently bound to a solid support is preferably allowed to incubate for 1–20 min. before effecting immunoreaction.

In the present invention the immunoreactant means any antigen or antibody optionally covalently, etc., attached to other molecules such as proteins or synthetic or natural polymers, etc. and the complementary immunoreactant means any antibody or antigen optionally covalently, etc., attached to other molecules such as synthetic or natural polymers, etc. capable of specifically binding to the immunoreactant. Generally, the immunoreactant is the species being sought out or quantified and the complementary immunoreactant is the known species used to find or quantify the immunoreactant. Certain immunoassays, etc. may not require such an arrangement, however. Examples of immunoreactants and complementary immunoreactants include the following:

| | |
|---|---|
| AFP | Alpha-fetoprotein |
| Beta-2-microglogulin | |
| CEA | Carcinoembryonic antigen |
| Ferritin | |
| CA 19–9 | Carbohydrate antigen 19–9 |
| PAP | Prostatic acid phosphatase |
| PSA | Prostate-specific antigen |
| CRP | C-reactive protein |
| Mb | Myoglobin |
| RF | Rheumatoid factor |
| ASO | Anti-streptolysin-O |
| FDP | Fibrin degradation product |
| Anti-thrombin-III | |
| Plasminogen | |
| Alpha-2-plasmin inhibitor | |
| D-dimer | Fibrin degradation product D-fragment dimer |
| IgG | Immunoglobulin G |
| IgA | Immunoglobulin A |

| | |
|---|---|
| IgM | Immunoglobulin M |
| IgE | Immunoglobulin E |
| C3 | Complement 3 |
| C4 | Complement 4 |
| Urinary albumin | |
| hCG | human chorionic gonadotropin |
| hPL | Human placental lactogen |
| Insulin | |
| HBs antigen | Hepatitis-B surface antigen |
| HBs antibody | Anti-hepatitis-B core antigen antibodies |
| HBc antibody | Anti-hepatitis-B core antigen antibodies |
| HCV antibody | Anti-hepatitis-C virus antibodies |
| Treponema | Anti-treponema pallidum antibodies |
| TSH | Thyroid stimulating hormone |
| LH | Lutenizing hormone |
| FSH | Follicle stimulating hormone |
| Digoxin | |
| Digitoxin | |
| Quinidine | |
| Procainamide | |
| NAPA | N-acetyl procainamide |
| Theophylline | |
| Phenytoin | |
| Phenobarbital | |
| Carbamazepine | |
| Valproic acid | |
| Ethosuccimide | |
| Gentamicin | |
| Tobramycin | |
| Amikacin | |
| Vancomycin | |
| Cyclosporin-A | |
| B12 | Vitamin B12 |
| Folic acid | |
| T3 | Triiodothyronine |
| T4 | Thyroxine |
| Estrogen | |

The immunoreactant, complementary immunoreactant, either, both, or neither may be adsorbed or covalently bound to a solid support and, in fact, all of the above-identified species can be called either an immunoreactant or a complementary immunoreactant depending on their role in the immunoassay. Pairing is important, the name is not, and where only an immunoreactant is referred to herein any of the above species and similar known species are meant. Naturally, all immunoreactants complimentary to those listed above are included in the present invention. Solid supports, etc., bearing immunoreactants on their surfaces, etc., are described as sensitized solid supports. If no solid support is used, a solution containing a known immunoreactant is described as a sensitized solution.

All immunoassays currently known can be improved by use of the above-described non-specific reaction suppressor. In particular, immunoagglutination assays such as hemagglutination or latex agglutination tests, adsorption onto the solid phase immunoassays or labeled antigen/antibody solid phase immunoassays like radioimmunoassays (RIAs), enzyme immunoassays (EIAs) and fluorescent immunoassays (FIAs), etc. are improved through the use of the invention non-specific reaction suppressor. Other useful immunoassays include chemiluminescent assays, immunochromatography, immunosensing, immuno-diffraction grating, etc.

The kit according to the present invention comprises first and second containers, the first container containing a solid support sensitized with an immunoreactant, the second container containing the above-described non-specific reaction suppressor.

The following examples illustrate the invention. However, it is to be understood that these examples in no way limit the invention.

EXAMPLE 1

Digoxin microparticle reagent preparation

A digoxin particle reagent is prepared from digoxin-human serum albumin (digoxin-HSA) conjugate according to the method of T. W. Smith et al. in *Biochemistry*, 9, 331 (1970) (incorporated herein by reference). The digoxin reagent is coupled to carboxylate-modified latex particles having a 0.292 μm diameter, by first subjecting the latex particles to ion exchange in a mixed-bed ion exchange resin (Bio Rad AG 501-X8) with stirring for two hours at room temperature. After ion exchange the latex particles are filtered and ready for coupling.

To a 50 ml polycarbonate centrifuge tube is added 50 ml of 0.1M bicarbonate buffer, pH 8.0 and 5 ml of a 10 wt. % latex particle suspension of the particles described above. The particles are incubated at 37° C. for 10 minutes with stirring prior to reaction. Then, 5 ml of 88 mg/ml 1-ethyl-3-(3-dimethylaminopropyl)-carbodiimide hydrochloride (EDC) freshly dissolved in water is added to the mixture and allowed to stand for 10 minutes. Thereafter, 2.5 ml of the 10 mg/ml digoxin-HSA conjugate is added thereto with vigorous stirring and incubated for 10 minutes. Coupling is stopped by adding 5 ml of 500 mM glycine buffer, pH 8.5. Another 10 minute incubation is done to ensure complete termination of reaction.

The digoxin-HSA conjugate coupled latex is centrifuged at 26000×g for 20 minutes. The supernatant is discarded, and to the pellet is added 25 ml of water. The pellet is resuspended with vigorous stirring. Washing is repeated four times, and, in the last resuspension washing step, 0.05% sodium azide solution is used as storage medium. Finally, the latex suspension is sonicated and diluted to the concentration (normally 0.1–0.4 wt. %) desired for use.

Anti-digoxin antibody buffer reagent composition

EDU solution was prepared by dissolving 2M of EDC into water, followed by hydrolysis, and added to the reagent described below in the listed amount after hydrolysis was confirmed.

An anti-digoxin antibody reagent is prepared by dissolving the following materials in water and adjusting the pH with hydrochloric acid.

| | |
|---|---|
| 3.68% | NaCl |
| 200 mM | Tris-(hydroxy)-aminomethane, pH 7.5 |
| 1.2% | Sodium dextransulfate |
| 8.0% | Choline chloride |
| 25 mM | EDU |
| 1 mg/ml | HSA (human sreum albumin) |
| 0.05% | Sodium azide |
| 1:120,000 | Diluted anti-digoxin monoclonal antibody (obtained from Beckman (preferably added last.) |

Assay conditions for sample evaluation

An LPIA-100 instrument (an immunoassay analyzer measuring turbidity as a function of time, made by Mitsubishi Kasei Corporation) was used for the test in the condition stated below. First, a calibration curve was established using calibrators having 0, 1, 2, 3 and 5 ng/ml of Digoxin (Roche Diagnostic Systems). 200 digoxin serum samples which had already been evaluated by radioimmunoassay (RIA, Dinabbott Corp., Japan) and determined to have concentrations from about 0 to 3 ng/ml were then evaluated with the LPIA-100 instrument, and the rate data from the LPIA instrument was plotted versus the known (by RIA) digoxin concentration both with and without EDU (25 mM) in solution, and this plot was compared to the calibration curve.

| Wavelength | 650 nm |
|---|---|
| Sample volume | 10 μl |
| Pushing buffer | 50 μl |
| Antibody reagent | 200 μl |
| Latex reagent | 40 μl |

Results of the tests

As is seen in FIGS. 1a–e and 2a–e, by comparing 1a to 2a, 1b to 2b, etc. the addition of EDU resulted in a dramatic improvement on the LPIA-100 data distribution; the sample data distribution became much more accurate and reliable in the presence of EDU. In particular, severe outliers were eliminated and sample accuracy and reliability were improved. The five graphs a–e are used to represent 200 points—40 points per graph—each point assigned at random to better show all the data and avoid overlap.

EXAMPLE 2

In order to show that the non-specific reaction suppressors of the invention do not effect, or effect only slightly, specific immunoreactant-complimentary immunoreactant reactions while eliminating or reducing non-specific reactions, the following experiment was carried out.

Preparation of anti-HBs antibody F(ab')$_2$ coated latex particle reagent

The IgG fraction of anti-hepatitis-B surface antigen (HBs) antibody was digested with pepsin, then purified by Sephacryl® S-200 gel filtration column chromatography to provide the F(ab')$_2$ fragment of the antibody.

The F(ab')$_2$ was mixed with polystyrene latex particles in 0.1M Tris buffer, pH 8, then the mixture was centrifuged, and the supernatant was replaced with bovine serum albumin (BSA) solution to stabilize the particles.

Following several wash cycles by centrifugation, the particle pellet was finally resuspended and sonicated in storage medium, and, then, was ready for use as an anti-HBs antibody latex particle reagent.

Assay conditions for sample evaluation

The above particles were evaluated according to the following experiments using the LPIA-100 instrument as in EXAMPLE 1, except that Tris-saline buffer solution (pH 8.2) was used instead of antibody reagent and the wavelength used was 950 nm.

Experiments

1. Screening of non-specific agglutination samples.

Several normal serum specimens which were independently confirmed to be negative with HBs antigen by RIA were tested by LPIA without EDU, and the samples showing non-specific reaction (i.e. samples showing false positive results; samples 2, 8, 11 and 14) were selected.

Figure 3:
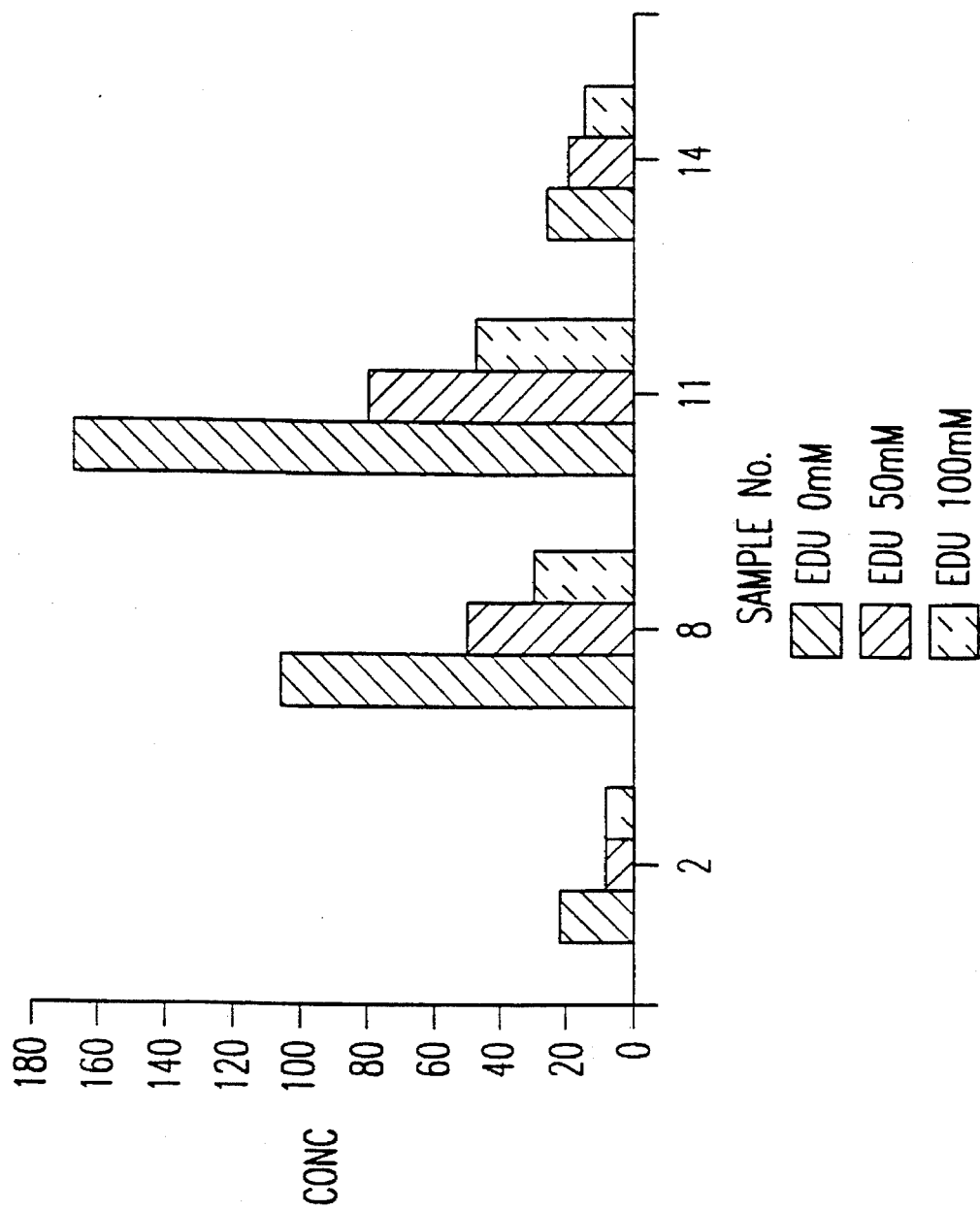
FIG. 3 shows the effect of an invention non-specific reaction suppressor on a Hepatitis-b samples showing non-specific reactions.

The selected false positive samples (i.e., samples with non-specific interactions) were then reanalyzed checked after incubation in the presence of 0, 50, and 100 mM EDU by LPIA. FIG. 3 shows the results.

Finally, the effect of EDU on immunoassay reactivity was checked with HBs surface antigen calibration standards in order to determine whether EDU was specific against non-specific reactions or whether it simply decreased reagent reactivity.

Samples with known amounts of HBs surface antigen and with different concentrations of EDU were tested against a calibration curve made with no EDU. Even in the case of 100 mM EDU, only a 15% reactivity drop was noted.

Based on the above experiments it is clear that EDU has a strong preventive effect against non-specific agglutination and does not effect, or effects to only a minor extent, specific immunoreactant-complimentary immoreactant interactions.

EXAMPLE 3

Preparation of a human serum albumin (HSA) coated microplate

A carboxylate modified microplate (Sumitomo Bakelite) was sensitized with HSA using EDC by methods known in the art.

Assay system to evaluate the effect of added EDU

Six outliers showing non-specific reactions taken from the digoxin non-specific reaction screening (no added EDU) described in EXAMPLE 1 (samples 5, 7, 18, 38, 46 and 65) and two normal (non-outlier) samples (NC1 and NC2) were tested as follows:

30 fold diluted serum samples were incubated with the microplate for 60 minutes. After several washes, 3000 fold diluted rabbit anti-human immunoglobulins antibody was reacted with the plate for 60 minutes. Again the plate was washed several times, then alkaline phosphatase-labeled goat anti-rabbit immunoglobulin was reacted in the plate for 60 minutes.

After the final wash, a solution of color generating substrate for alkaline phosphatase was added into the plate, and the existence and amount of human immunoglobulins was detected according to the intensity of the color. The effect of EDU addition was tested by diluting samples with a diluent containing 50 mM EDU.

Results

Figure 4:
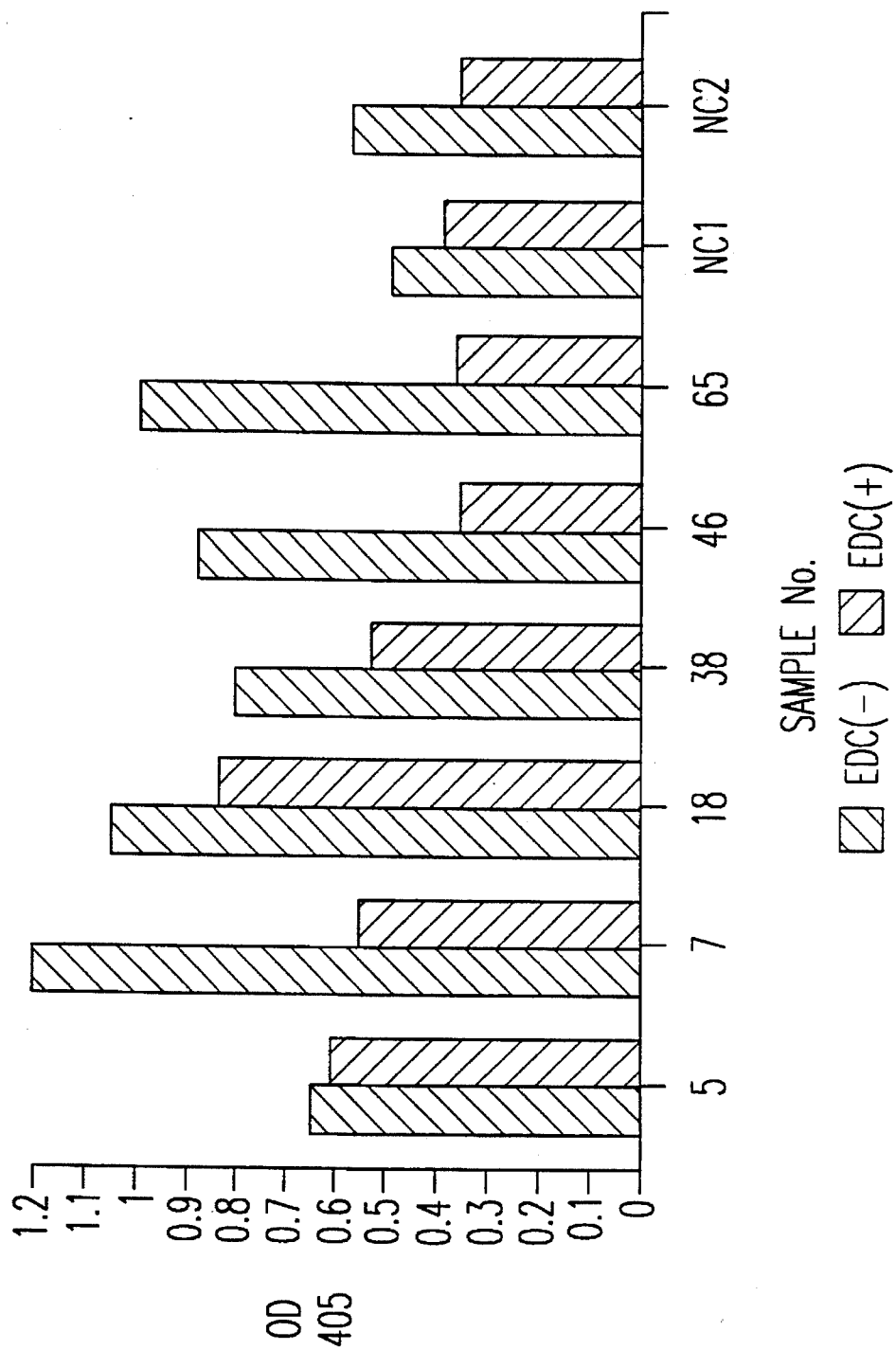
FIG. 4 shows the reduction of non-specific reactions when a non-specific reaction suppressor according to the present invention is utilized in an immunoassay using human serum albumin coated microplates.

As is seen in FIG. 4, the addition of EDU significantly reduced the relatively high immunoglobulin attachment to the microplate in the case of the outliers (non-specific reaction samples). The normal samples showed reduced immunoglobulin binding without EDU and did not change much in the presence of EDU. Thus, the presence of EDU significantly reduces the non-specific binding of immunoglobulin on a solid plate support, decreasing false positive results. Thus, the effectiveness of the invention materials on e.g., microplate enzyme immunoassays, etc. is demonstrated.

EXAMPLE 4

Figure 5:
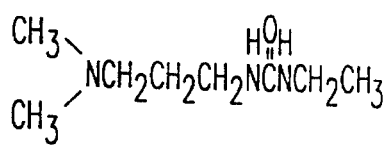
FIG. 5 shows the structure of 11 compounds used in Example 4 to determine non-specific reaction suppressing ability.
Figure 5:
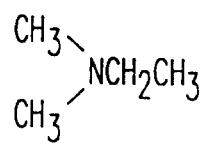
Figure 5:
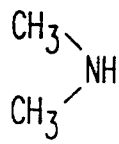
Figure 5:
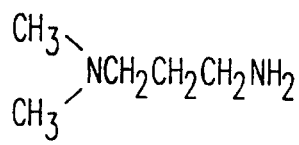
Figure 5:
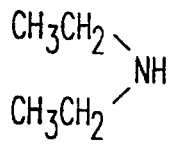
Figure 5:
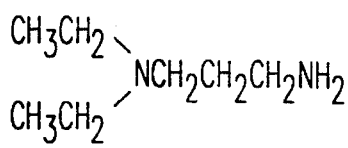
Figure 5:
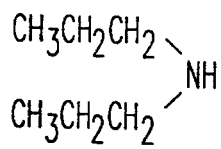
Figure 5:
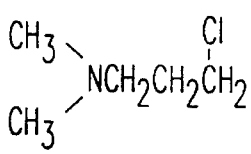
Figure 5:
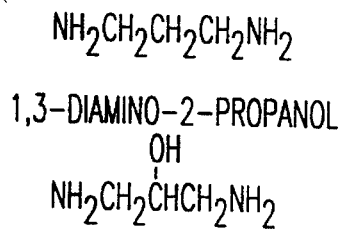
Figure 5:
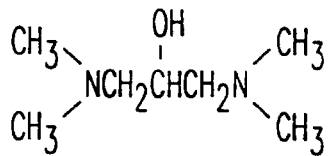

The eleven compounds shown in FIG. 5 were added to three samples (HR1, HR2 and HR3) showing non-specific reactions (i.e., outliers from Example 1) and tested on the LPIA-100 system as in Example 1. Table 1 shows the results. The numbers in the Table show relative reactivity as % values, where 100% corresponds to the expected reactivity based on the calibration curves shown in FIGS. 1 and 2.

From the results in Table 1, it is clear that the secondary and tertiary amines according to the invention decrease non-specific reactions whereas primary amines behave much more poorly.

TABLE 1

| | HR1 | HR2 | HR3 |
|---|---|---|---|
| | EDU | | |
| 0 mM | 159.0 | 148.5 | 110.3 |
| 2.5 mM | 138.2 | 132.4 | 107.6 |

TABLE 1-continued

|  | HR1 | HR2 | HR3 |
|---|---|---|---|
| 5 mM | 119.1 | 120.4 | 108.0 |
| 10 mM | 105.6 | 110.8 | 106.9 |
| 20 mM | 95.3 | 100.0 | 104.8 |
| Dimethylamine | | | |
| 0 mM | 159.0 | 148.5 | 110.3 |
| 1.25 mM | 130.7 | 128.5 | 107.5 |
| 2.5 mM | 125.1 | 122.9 | 106.0 |
| 5 mM | 126.7 | 118.8 | 103.5 |
| 10 mM | 133.8 | 123.0 | 106.8 |
| 20 mM | 134.9 | 121.3 | 108.8 |
| Diethylamine | | | |
| 0 mM | 159.0 | 148.5 | 110.3 |
| 1.25 mM | 132.5 | 130.0 | 107.5 |
| 2.5 mM | 123.7 | 123.9 | 105.5 |
| 5 mM | 128.3 | 120.7 | 105.6 |
| 10 mM | 130.9 | 119.9 | 105.5 |
| 20 mM | 135.3 | 119.0 | 106.9 |
| Dipropylamine | | | |
| 0 mM | 159.0 | 148.5 | 110.3 |
| 1.25 mM | 134.2 | 133.3 | 109.9 |
| 2.5 mM | 128.4 | 127.6 | 104.6 |
| 5 mM | 123.3 | 125.8 | 105.7 |
| 10 mM | 126.9 | 128.6 | 105.2 |
| 20 mM | 135.7 | 130.9 | 106.9 |
| Dimethylethylamine | | | |
| 0 mM | 159.0 | 148.5 | 110.3 |
| 1.25 mM | 136.4 | 125.9 | 111.4 |
| 2.5 mM | 122.8 | 118.2 | 106.9 |
| 5 mM | 109.5 | 111.0 | 106.4 |
| 10 mM | 105.5 | 108.3 | 108.3 |
| 20 mM | 99.6 | 104.4 | 108.4 |
| Dimethylaminopropylamine | | | |
| 0 mM | 159.0 | 148.5 | 110.3 |
| 1.25 mM | 128.8 | 123.5 | 104.9 |
| 2.5 mM | 131.2 | 126.1 | 104.8 |
| 5 mM | 129.3 | 124.4 | 106.6 |
| 10 mM | 123.6 | 121.5 | 110.0 |
| 20 mM | 111.6 | 111.3 | 107.8 |
| Diethylaminopropylamine | | | |
| 0 mM | 159.0 | 148.5 | 110.3 |
| 1.25 mM | 137.3 | 133.0 | 108.9 |
| 2.5 mM | 132.9 | 127.2 | 107.0 |
| 5 mM | 135.5 | 127.4 | 106.7 |
| 10 mM | 128.4 | 127.3 | 110.3 |
| 20 mM | 118.6 | 123.1 | 118.3 |
| Dimethylaminopropylchloride | | | |
| 0 mM | 159.0 | 148.5 | 110.3 |
| 1.25 mM | 129.2 | 126.2 | 106.3 |
| 2.5 mM | 122.5 | 119.2 | 102.0 |
| 5 mM | 111.9 | 112.1 | 105.1 |
| 10 mM | 103.2 | 102.8 | 102.5 |
| 20 mM | 92.5 | 88.9 | 88.7 |
| Bis-dimethylamino-propanol | | | |
| 0 mM | 159.0 | 148.5 | 110.3 |
| 1.25 mM | 175.5 | 159.5 | 115.9 |
| 2.5 mM | 163.3 | 150.6 | 109.3 |
| 5 mM | 160.6 | 145.1 | 112.2 |
| 10 mM | 142.7 | 131.4 | 116.4 |
| 20 mM | 126.0 | 118.8 | 117.6 |
| Diaminopropane | | | |
| 0 mM | 159.0 | 148.5 | 110.3 |
| 1.25 mM | 183.9 | 172.9 | 111.4 |
| 2.5 mM | 184.8 | 170.2 | 110.7 |
| 5 mM | 194.7 | 177.0 | 109.6 |
| 10 mM | 235.1 | 206.9 | 112.9 |
| 20 mM | 351.8 | 273.2 | 110.6 |
| Diaminopropanol | | | |

TABLE 1-continued

|  | HR1 | HR2 | HR3 |
|---|---|---|---|
| 0 mM | 159.0 | 148.5 | 110.3 |
| 1.25 mM | 177.1 | 170.0 | 112.1 |
| 2.5 mM | 172.9 | 165.2 | 107.9 |
| 5 mM | 188.7 | 173.9 | 108.2 |
| 10 mM | | | |
| 20 mM | | | |

Obviously, numerous modifications and variations of the present invention are possible in light of the above teachings. It is therefore to be understood that within the scope of the appended claims, the invention may be practiced otherwise than as specifically described herein.

What is claimed is:

1. A composition useful for immunoassays comprising a solid support having an immunoreactant covalently bound thereto or adsorbed thereon and selected from the group consisting of antigens and antibodies and a non-specific reaction suppressor of the formula:

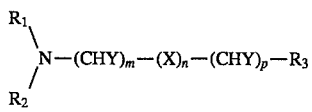

wherein X is —NH—(CO)—NH—, —NH—(CS)—NH—, or —N=C=N—, $R_1$ and $R_2$, which may be the same or different, are $C_1$–$C_5$ linear or branched alkyl groups, or $R_1$ and $R_2$, together with nitrogen, is

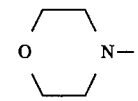

or the metho-p-toluenesulfonate salt thereof,

Y, which may be the same or different, is any of H, OH and halogen, $R_3$ is —$NR_1R_2$, —$NH_2$, —CHY, cyclohexyl, or H, m is an integer of from 2 to 5, p is an integer of from 0 to 5, and n is 0 or 1, and the acid addition salts thereof.

2. The composition of claim 1, further comprising an aqueous solvent.

3. The composition of claim 1, further comprising a complimentary immunoreactant which specifically binds with said immunoreactant.

4. The composition of claim 2, wherein said non-specific reaction suppressor is present in from 0.1 to 300 mM based on the volume of aqueous solvent.

5. The composition of claim 1 wherein said solid support is a latex particle, said immunoreactant is coupled to said latex particle with 1-ethyl-3-(3-dimethylaminopropyl) carbodiimide, and said non-specific reaction suppressor is 1-ethyl-3-(3-dimethyl-aminopropyl)urea.

6. The composition of claim 1 wherein said non-specific reaction suppressor is 1-ethyl-3-(3-dimethylaminopropyl)urea or 1-cyclohexyl-3-3(2-morpholinoethyl)urea metho-p-toluenesulfonate.

7. The composition of claim 1, wherein the non-specific reaction suppressor is selected from the group consisting of N,N-dimethylethylamine, 3-dimethylaminopropylamine, 3-diethylaminopropylamine, dimethylaminopropylchloride, and 1,3-bis(dimethylamino)-2-propanol.

8. A kit comprising first and second container means, said first container means containing a solid support having an immunoreactant covalently bound thereto or adsorbed thereon and selected from the group consisting of antigens and antibodies, said second container means containing a non-specific reaction suppressor of the formula:

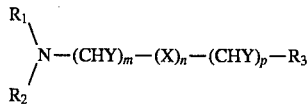

wherein X is —NH—(CO)—NH—, —NH—(CS)—NH—, or —N═C═N—, $R_1$ and $R_2$, which may be the same or different, are $C_1$-$C_5$ linear or branched alkyl groups, or $R_1$ and $R^2$, together with nitrogen, is

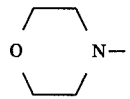

or the metho-p-toluenesulfonate salt thereof,

Y, which may be the same or different, is any of H, OH and halogen, $R_3$ is —$NR_1R_2$, —$NH_2$, —CHY, cyclohexyl, or H, m is an integer of form 2 to 5, p is an integer of from 0 to 5, and n is 0 or 1, and the acid addition salts thereof.

9. In an immunoassay method, the improvement comprising the step of adding a non-specific reaction suppressor of the formula:

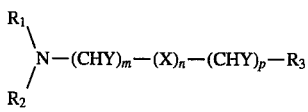

to a sample to be tested, to a solid support, having an immunoreactant covalently bound thereto or adsorbed thereon and selected from the group consisting of antigens and antibodies or to both a sample to be tested and a solid support having an immunoreactant covalently bound thereto or adsorbed thereon and selected from the group consisting of antigens and antibodies, wherein X is —NH—(CO)—NH—, —NH—(CS)—NH—, or —N═C═N—, $R_1$ and $R_2$, which may be the same or different, are $C_1$-$C_5$ linear or branched alkyl groups, or $R_1$ and $R^2$, together with nitrogen, is

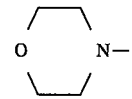

or the metho-p-toluenesulfonate salt thereof,

Y, which may be the same or different, is any of H, OH and halogen, $R_3$ is —$NR_1R_2$, —$NH_2$, —CHY, cyclohexyl, or H, m is an integer of from 2 to 5, p is an integer of from 0 to 5, and n is 0 or 1, and the acid addition salts thereof.

10. The method of claim 9, wherein said immunoassay method is an agglutination assay.

11. The method of claim 10, wherein said non-specific reaction suppressor is 1-ethyl-3-(3-dimethylaminopropyl)urea.

12. The method of claim 9, wherein said non-specific reaction suppressor is selected from the group consisting of N,N-dimethylethylamine, 3-dimethylaminopropylamine, 3-diethylaminopropylamine, dimethylaminopropylchloride, and 1,3-bis(dimethylamino)-2-propanol.

13. The composition as claimed in claim 1, wherein n is 1.

14. The composition as claimed in claim 1, where $R_1$ and $R_2$, together with nitrogen, is

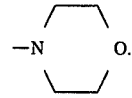

15. The composition as claimed in claim 1, wherein $R_3$ is —$NR_1R_2$, —$NH_2$ or cyclohexyl.

16. The composition as claimed in claim 1, wherein $R_3$ is —CHY.

* * * * *